US006280939B1

(12) United States Patent
Allen (10) Patent No.: US 6,280,939 B1
(45) Date of Patent: Aug. 28, 2001

(54) METHOD AND APPARATUS FOR DNA SEQUENCING USING A LOCAL SENSITIVE FORCE DETECTOR

(75) Inventor: Michael J. Allen, Santa Barbara, CA (US)

(73) Assignee: Veeco Instruments, Inc., Plainview, NY (US)

( * ) Notice: Subject to any disclaimer, the term of this patent is extended or adjusted under 35 U.S.C. 154(b) by 0 days.

(21) Appl. No.: 09/145,352

(22) Filed: Sep. 1, 1998

(51) Int. Cl.[7] ........................................... C12Q 1/68
(52) U.S. Cl. ................................. 435/6; 435/91.1
(58) Field of Search ..................... 435/6, 91.1; 536/25.3

(56) References Cited

U.S. PATENT DOCUMENTS

| 5,077,473 | 12/1991 | Elings et al. | 250/306 |
| 5,081,390 | 1/1992 | Elings | 310/328 |
| 5,266,801 | 11/1993 | Elings et al. | 250/306 |
| 5,412,980 | 5/1995 | Elings et al. | 73/105 |
| 5,519,212 | 5/1996 | Elings et al. | 250/234 |
| 5,620,854 | 4/1997 | Holzrichter et al. | 435/6 |

OTHER PUBLICATIONS

Direct Observation of Enzyme Activity with the Atomic Force Microscope, Radmacher et al., Science, vol. 265, pp. 1577–1579, Sep. 1994.

Atomic Force Microscope of Biomolecules, Hansma, J. Vac. Sci. Technol., vol. B 14(2), pp. 1390–1394, Mar./Apr. 1996.

Nanoscope® Atomic Force Microscopes: Applications for the Biological Sciences, Digital Instruments brochure, Nov., 1996.

*Escherichia coli* RNA Polymerase Activity Observed Using Atomic Force Microscopy, Kasas et al., Biochemistry, vol. 36(3), pp. 461–468, Jan. 1997.

A New Method for Sequencing DNA, Maxam and Gilbert, Proc. Natl. Acad. Sci. USA, vol. 74(2), pp. 560–564, Feb. 1977.

DNA Sequencing with Chain–terminating Inhibitors, Sanger et al., Proc. Natl. Acad. Sci. USA, vol. 72(12), pp. 5463–5467, Dec. 1977.

DNA Replication, Kornberg & Baker, (2nd ed.) pp. 106–109, (1992).

A Rapid Method for Determining Sequences in DNA by Primed Synthesis with DNA Polymerase, F. Sanger & A.R. Coulson, J. Mol. Biol. vol. 94, pp. 441–448 (1975).

*Primary Examiner*—Ardin H. Marschel
(74) *Attorney, Agent, or Firm*—Nilles & Nilles, S.C.

(57) ABSTRACT

DNA sequencing is performed in real time using an atomic force microscope (AFM). The AFM's probe detects motions that occur when a polymerase incorporates nucleotides into a growing polynucleotide chain and a newly formed double-stranded polynucleotide helix translocates (or "ratchets") through the polymerase's reaction site. These motions generate a mechanical force that is reflected, either directly or indirectly, by motion of the AFM cantilever. The resulting changes in cantilever motion are detected and can be recorded as an indication that a nucleotide has been incorporated into the DNA template. To determine which nucleotide type has been incorporated, a characteristic of the incorporation of at least one nucleotide type of interest is flagged so as to be distinguishable from the corresponding characteristics of the incorporation of nucleotides of other types. In a preferred embodiment, the average incorporation delay for nucleotides of the nucleotide type of interest are flagged such that the average incorporation delay for nucleotides of the nucleotide type of interest is unique when compared to the average incorporation delay of nucleotides of other nucleotide types.

28 Claims, 4 Drawing Sheets

METHOD AND APPARATUS FOR DNA SEQUENCING USING A LOCAL SENSITIVE FORCE DETECTOR

BACKGROUND OF THE INVENTION

1. Field of the Invention

The present invention relates generally to methods and apparatus for detecting nucleotide incorporation, and more particularly to a method and apparatus for detecting nucleotide incorporation into a growing polynucleotide chain. The invention is particularly well suited for rapid, automated DNA sequencing.

2. Discussion of the Related Art

Deoxyribonucleic acid (DNA) is composed of four different types of bases: adenine (A), guanine (G), cytosine (C), and thymine (T). A base together with a phosphate and a sugar molecule form a nucleotide. In a DNA molecule, the bases are arranged along a sugar-phosphate backbone to form a chain. These chains are often referred to as "DNA strands." Two DNA strands pair up to form a double-stranded DNA molecule. The strands pair up due to hydrogen bonding between complementary bases. The nucleotide composition and order of a given DNA strand are represented in a DNA sequence. For example, "CCGAT" is a DNA sequence.

DNA sequencing is important for a variety of tasks, including basic scientific research, medical studies, diagnostics, and genome projects. For these tasks, rapid DNA sequencing methods are desirable. However, the speed of previous DNA sequencing methods has been significantly limited by several factors including time and labor for subcloning long DNA fragments into sequencing vectors, sequencing chemistries, and DNA fragment separation techniques, as well as sequence data reading.

Current DNA sequencing techniques are based on the generation of a plurality of DNA fragments corresponding to the sequence of a DNA template. One such DNA sequencing technique is disclosed in Maxam and Gilbert, "A New Method for Sequencing DNA," *Proc. Natl. Acad. Sci. USA*, Vol. 74(2), February 1977, where a DNA template of interest is chemically degraded to produce a plurality of DNA fragments corresponding to the DNA sequence. Another DNA sequencing technique is disclosed in Sanger et. al., "DNA Sequencing with Chain-terminating Inhibitors," *Proc. Natl. Acad. Sci. USA*, Vol. 74(12), December 1977, where a plurality of terminated DNA fragments complementary to a DNA template are synthesized. Both of these techniques require labeling the DNA fragments with a reporter, such as a radionucleotide label or a fluorescent label, and electrophoretically separating the labeled DNA fragments on a sieving matrix, such as a polyacrylamide. Sieving matrices are semi-porous materials that separate DNA based on the size of the DNA molecule. Typically, the sieving matrices are poured between two glass plates to form a gel. DNA is applied to one end of the gel, an electrical current is applied, and the negatively-charged DNA molecules travel through the gel toward the cathode, with the smallest DNA molecules traveling the farthest.

This process, called gel electrophoresis, has several drawbacks including (1) laborious gel pouring protocols and (2) variability in the gels due to cleanliness of gel plates, fluctuations in ambient temperature, and inconsistent qualities in gel reagents. This variability can alter the quality of the sequence data and even render the sequence data unusable. Furthermore, separating the DNA fragments requires electrophoresing the fragments at a speed slow enough to (1) permit detection of labeled fragments, (2) avoid decomposition of gel, and (3) allow for adequate separation of fragments. These time constraints limit the speed at which DNA sequencing can be performed using electrophoresis-based sequencing methods.

In sum, limitations of previous DNA sequencing techniques include the need for a reporter label, the time required for performing the techniques, and/or the variability in gels. In light of these limitations, alternative DNA sequencing methodologies are needed.

Atomic force microscopes (AFMs) recently have been used to study biomolecules, as described below. An AFM has a tip that is end-mounted on a flexible cantilever. Interactions between the tip and the sample influence the motion of the cantilever, and one or more parameters of this influence are measured to generate data representative of one or more properties of the sample. AFMs can be operated in different modes including contact mode, TappingMode, (Tapping and TappingMode are trademarks of Digital Instruments, Inc.), and non-contact mode. In contact mode, the cantilever is not oscillated, and cantilever deflection is monitored as the probe tip is dragged over the sample surface. In TappingMode, the cantilever is oscillated mechanically at or near its resonant frequency so that the probe tip repeatedly taps the sample surface, thus reducing the probe tip's oscillation amplitude. The oscillation amplitude indicates proximity to the sample surface and may be used as a signal for feedback. U.S. patents relating to Tapping and TappingMode include U.S. Pat. Nos. 5,266,801, 5,412,980, and 5,519,212, by Elings et al., all of which hereby are incorporated by reference. In the non-contact mode, attractive interactions between the probe tip and the sample (commonly thought to be due to Van der Waals' attractive forces) shift the cantilever resonance frequency when the probe tip is brought within a few nanometers of the sample surface. These shifts can be detected as changes in cantilever oscillation resonant frequency, phase, or amplitude, and used as a feedback signal for AFM control.

Whether operating in contact mode, TappingMode, or non-contact mode, feedback is typically used during AFM scanning to adjust the vertical position of the probe relative to the sample so as to keep the probe tip-sample interaction constant. A measurement of surface topography or another sample characteristic may then be obtained by monitoring a signal such as the voltage used to control the vertical position of the scanner. Alternatively, independent sensors may monitor the position of the tip during scanning to obtain a map of surface topography or another measured sample characteristic. Measurements can also be made without feedback by monitoring variations in the cantilever deflection as the probe moves over the surface. In this case, recording the cantilever motion while scanning results in an image of the surface topography in which the height data is quantitative. Additionally, the positioning of the AFM probe can be enhanced by compensating for drift. U.S. patents relating to drift compensation include U.S. Pat. Nos. 5,081,390 and 5,077,473 by Elings et al., both of which are hereby incorporated by reference.

Proposals have been made to use AFMs to study biomolecules. For instance, Radmacher et al., "Direct Observation of Enzyme Activity with the Atomic Force Microscope," *Science*, Vol. 265, Sept. 9, 1994, (Radmacher) proposes the use of an AFM to measure height fluctuations of an enzyme (lysozyme). Radmacher believed that the measured height fluctuations probably corresponded to motions of lysozyme during hydrolysis of a substrate oligoglycoside.

Other proposed uses of AFM to study biomolecules are disclosed in Hansma, "Atomic Force Microscopy of Biomolecules," *J. Vac. Sci. Technol.*, Vol. B 14(2), March/April 1996 (Hansma). Hansma lists several DNA applications including (1) calculation of persistence lengths for moving DNA molecules, (2) imaging DNA molecules as a nuclease degrades DNA, and (3) monitoring forces between DNA bases.

Still another proposal is disclosed in Kasas et. al., *Escherichia coli* RNA Polymerase Activity Observed Using Atomic Force Microscopy," *Biochemistry*, Vol. 36(3), Jan. 21, 1997 (Kasas). Kasas used an AFM to observe an RNA polymerase transcribing DNA templates in sequential AFM images. Kasas also noted that an RNA polymerase can maintain its biological activity when it is adsorbed onto mica.

While Radmacher, Hansma, and Kasas all disclose use of an AFM to study biomolecules, none of these publications disclose using an AFM to detect incorporation of a nucleotide into a growing polynucleotide chain. That is, these publications do not disclose using an AFM to determine the sequence of a DNA molecule.

Determining the sequence of a DNA molecule is, however, contemplated in U.S. Pat. No. 5,620,854 by Holzrichter. Holzrichter discloses use of an AFM to determine the sequence of a DNA template. The Holzrichter patent contains only a very limited discussion of varying concentrations of nucleotides, and has several shortcomings. First, it lacks a sufficient disclosure as to how to determine which of the four nucleotides is incorporated into the growing nascent DNA strand. In particular, Holzrichter proposes that each nucleotide addition reaction is different based on fact that different nucleotide types (e.g., As, Cs, Gs, and Ts) have different base pairing characteristics, and the method can distinguish nucleotides then based on differences in the number of hydrogen bonds. However, only two of four nucleotides have a different number of hydrogen bonds (A and T have two hydrogen bonds and G and C have three hydrogen bonds), and furthermore nucleotides cannot be easily distinguished based on these differences alone. Second, Holzrichter's process makes no correction for background noise. Third, the signal to noise ratio of Holzrichter's process is not high enough to determine which base was incorporated. Thus, Holzrichter does not enable a determination of which nucleotide is incorporated into the DNA template. Therefore, Holzrichter does not enable using an AFM for DNA sequencing or even for distinguishing nucleotide incorporation from other events, such as background movements of the polymerase not related to nucleotide incorporation.

OBJECTS AND SUMMARY OF THE INVENTION

An object of the invention is to use a local sensitive force detector to detect incorporation of a nucleotide of interest into a growing polynucleotide chain. In accordance with a first aspect of the invention, this object is achieved by (1) flagging at least one nucleotide type of interest such that its incorporation can be distinguished from the incorporation of other nucleotides and (2) detecting nucleotide incorporations during the polymerase reaction. Determining which nucleotide is incorporated permits sequencing of a growing polynucleotide chain.

Another object of the invention is to provide a method for DNA sequencing using a local sensitive force detector.

In accordance with another aspect of the invention, this process preferably comprises using an atomic force microscope (AFM) as the detector and operating the AFM in either contact mode, TappingMode, or non-contact mode.

Still another object of the invention is to provide a method for rapid DNA sequencing.

In accordance with still another aspect of the invention, this object is achieved by using an AFM to obtain real-time detection of incorporation of nucleotides into a growing polynucleotide chain during a polymerization reaction. The AFM probe tip is placed at a polynucleotide/polymerase complex. The probe tip detects motions that the polymerase undergoes when a growing polynucleotide chain, the growth of which is governed by base pair rules, translocates through a reaction site of the polymerase following nucleotide incorporation. The motions of the polymerase generate a force that is reflected, either directly of indirectly, by motion of the AFM cantilever.

Still another object is to provide a method for DNA sequencing without using a nucleotide label.

In accordance with still another aspect of the invention, this object is achieved by using an AFM placed at a DNA/polymerase complex to detect incorporation of nucleotides into a DNA template. Because motions that the polymerase undergoes indicate that a nucleotide is incorporated, no reporter label is required.

Another object of the invention is to provide a local sensitive force detector capable of reliably detecting the incorporation of a nucleotide of interest into a growing polynucleotide chain.

In accordance with still another aspect of the invention, this object is achieved by providing a local sensitive force detector that includes a probe and a detection device. The probe is configured to react to movement of a polymerase during a polymerase reaction in which 1) the polymerase reaction comprises nucleotides of more than one nucleotide type, 2) a chemical bond forms between a newly incorporated nucleotide and previously incorporated nucleotide, 3) the chemically bonded nucleotides extend a growing polynucleotide chain, and 4) a characteristic of the incorporation of at least one nucleotide type of interest is flagged during the reaction such that the incorporation of nucleotides of the nucleotide type of interest is distinguishable from incorporation of nucleotides of at least one other nucleotide type. The detection device monitors operation of the probe and is capable of detecting the movement of the growing polynucleotide chain through the polymerase during nucleotide incorporation.

The detection device preferably comprises a computer which is capable of transforming detected incorporation data into nucleotide data.

The local sensitive force detector preferably comprises an atomic force microscope (AFM).

BRIEF DESCRIPTION OF DRAWINGS

Preferred exemplary embodiments of the invention are illustrated in the accompanying drawings in which like reference numerals represent like parts throughout, and in which.

DETAILED DESCRIPTION OF THE PREFERRED EMBODIMENTS

1. Method Overview:

The present invention can be best understood by beginning with a brief discussion of nucleic acid polymerization. Nucleic acids are a family of macromolecules including DNA and RNA. Nucleic acid polymerization is an enzymatic reaction in which a complementary chain (also referred to as a strand) of nucleic acid is polymerized based on a polynucleotide template. The polymerase forms a complex with the polynucleotide template (polynucleotide/polymerase complex). This polynucleotide/polymerase complex usually includes, but is not limited to, a polymerase molecule plus at least one of the following: (1) a primed single-stranded DNA template, (2) a polynucleotide duplex with gaps or single-stranded protruding 5' termini, (3) a nicked double-stranded DNA, (4) an unprimed single-stranded DNA (hairpin), or (5) a single-stranded RNA. The growing polynucleotide chain usually (but not necessarily) comprises a DNA molecule. Accordingly, this application will discuss polymerization reactions in which the polynucleotide comprises a DNA molecule. However, it should be understood that the invention also is applicable to other polynucleotides, such as RNA.

During a polymerization reaction, at least the portion of the DNA molecule that is serving as a DNA template is in a single-stranded state, normally (but not necessarily) due to disassociation of a double-stranded DNA molecule. Incorporation of nucleotides is performed under base pair rules, where, in DNA, G and C always pair with one another, and A and T always pair with one another. In RNA, G and C always pair with one another, and U and A always pair with one another. The polymerization reaction is driven by a type of enzyme, called a polymerase, which contains a reaction site.

The at least partially single-stranded DNA template rests in the reaction site, with a single location of the DNA template available for nucleotide incorporation. At the reaction site, the polymerase sequentially incorporates nucleotides into a growing DNA chain. The order of the nucleotides in the growing polynucleotide chain is governed by the DNA template and base pair rules. Following the base pair rules, when an appropriate nucleotide comes into contact with the template, the polymerase incorporates the new nucleotide into the growing chain by forming a 3', 5'-phosphodiester bond between the previously incorporated nucleotide and the newly incorporating nucleotide. This bond formation involves the hydrolysis of the phosphate bond on the newly incorporating nucleotide and bond formation with the 3'-OH of the previously incorporated nucleotide of the growing DNA chain. This growing chain is hydrogen bonded to the DNA template to form a double-stranded DNA helix. Next, the newly formed double-stranded DNA helix translocates through the reaction site. This translocation moves the double-stranded DNA out of the reaction site, shifting the single-stranded template over one nucleotide and placing a subsequent location in the DNA template in the reaction site. Thus, nucleotide incorporation is sequential.

Time necessarily elapses between the incorporation of one nucleotide and the incorporation of the next nucleotide because, as described above, incorporations do not occur simultaneously. This elapse of time between incorporations can be characterized as a "delay." Assuming a particular nucleotide concentration, delays in nucleotide incorporations are fairly uniform, with some variability. Thus, it is appropriate to speak of an "average incorporation delay." Therefore, depending upon reaction-specific factors such as reaction temperature and the concentration of a given nucleotide in the solution, a polymerization reaction for a particular type of nucleotide (e.g., A, C, T, or G) could have an average incorporation delay of a specific time.

The double-stranded DNA molecule additionally comprises two antiparallel strands, where one strand is in the so-called 5'→3' orientation and the other strand is in the so-called 3'→5' orientation. These two antiparallel strands are said to be the reverse complement of each other. That is, the strands have the same sequence when (1) one is read left to right and the other is read right to left (i.e., one is reversed), and (2) the complementary bases are substituted. DNA is polymerized in the 5'→3' direction, with nucleotides added to the 3'-OH end of the strand. DNA nucleotides are generically abbreviated as dNTPs (or deoxynucleoside triphosphates). The enzyme has two substrates: the growing chain containing a free 3'-OH and a dNTP. It should be understood that whenever this application refers to a DNA sequence, it is meant to be in the 5'→3' orientation. Applying these rules to a DNA template of 5'-CCGAT-3', the newly synthesized, reverse complement strand will be 5'-ATCGG-3'. This DNA molecule can be schematically represented as follows:

During a polymerization reaction many motions or movements occur, including (but not limited to) those of the polymerase and those of the growing DNA chain. The polymerase moves during polymerization due to events including (but not limited to) (1) nucleotide incorporation and (2) translocation of the newly-formed double-stranded DNA helix out of the reaction site. Specifically, the polymerase moves when the nucleotide enters the reaction site during the incorporation. Additionally, the polymerase moves to accommodate ratcheting movement of the newly-formed, bulkier, double-stranded DNA helix out of the reaction site. These polymerase motions include (but are not limited to) conformational changes (e.g., changes in shape or size) that the polymerase undergoes during the polymerase reaction. These motions are akin to the motions that a body undergoes during breathing, where the chest expands and contracts to accomodate the volume of air present in the lungs. Additionally, the DNA itself is moving, including the ratcheting movement through the polymerase. The motions indicate that a nucleotide has been incorporated into the growing DNA chain.

The present invention involves using a local sensitive force detector to detect motions of the polymerase during nucleotide incorporation into a growing polynucleotide chain during a polymerization reaction. The present invention is additionally concerned with determining the sequence of a DNA template. The detector minimally requires a probe and a detection device for detecting effects of polymerase movements at the probe. Such detectors used in the art include scanning probe microscopes (SPMs) including atomic force microscopes (AFMs) and instruments comprising a local force detector plus a laser or other optical device, such as an interferometer, or other devices such as piezoresistive or capacitive force/position sensors. The invention will be described primarily in conjunction with an AFM, it being understood that it is applicable to other local force detectors as well.

Figure 1:
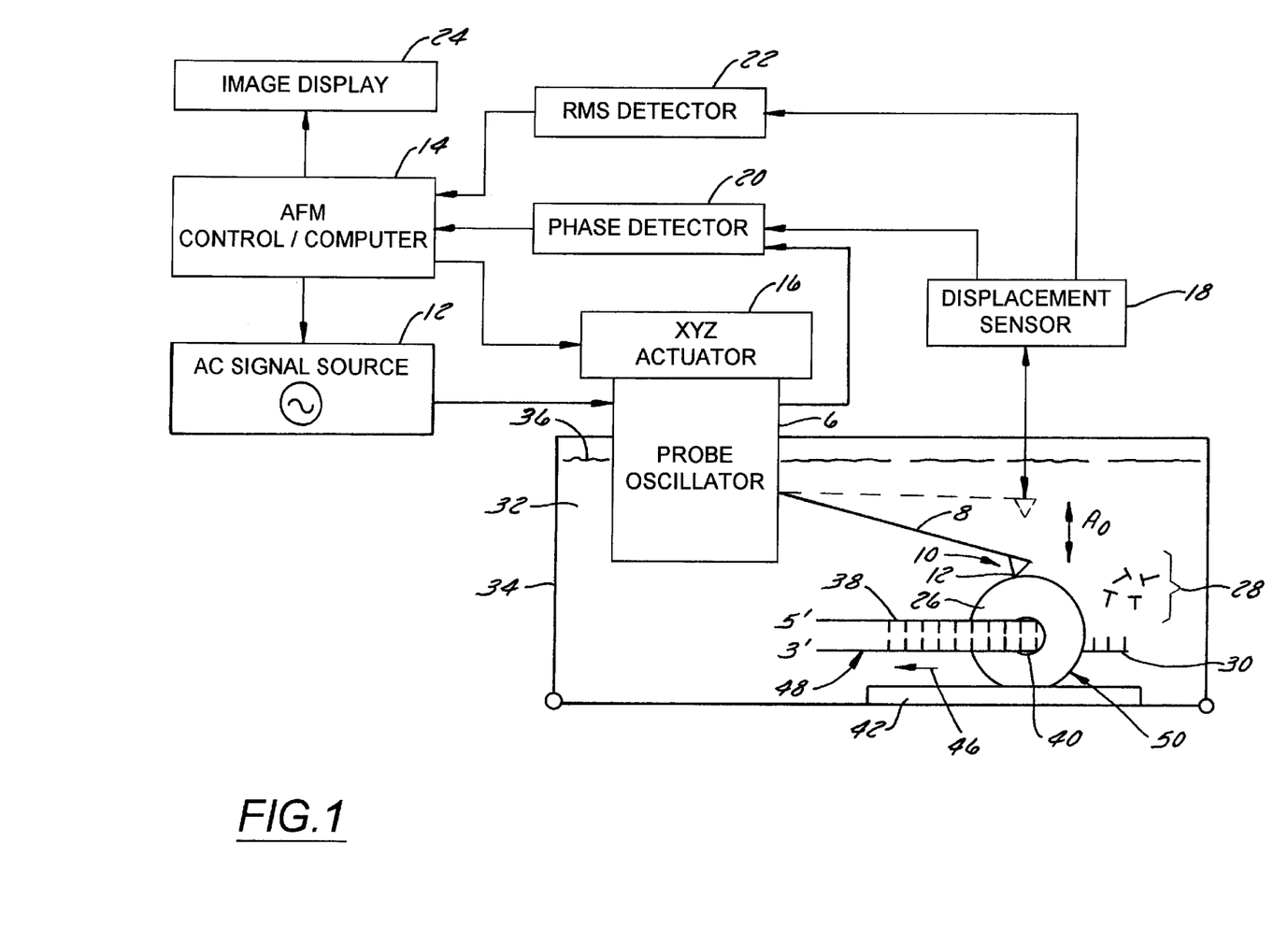
FIG. 1 is a schematic plan view of a local force detector for detecting motions of a polymerase molecule during nucleotide incorporation into a growing polynucleotide chain during a polymerization reaction.

A preferred embodiment of an AFM usable in the invention is illustrated in FIG. 1. The AFM includes a probe 10 controlled by a computer 14 to detect motions of a polymerase 26 by intermittent or other contact with it, or by using a "non-contact" technique. If the AFM operates in an oscillating mode, the probe 10 may be oscillated by an oscillator 6, which can drive the probe 10 appropriately, usually at or near the probe's resonant frequency. The probe 10 includes 1) a cantilever 8 having a base fixed to the oscillator 6 and a free end and 2) a probe tip 12 mounted on the cantilever 8. An electronic signal is applied, under control of the computer 14, from an AC signal source (not shown) to the oscillator 6 to drive the probe tip 12 to oscillate at a free oscillation amplitude $A_0$ (assuming that the AFM is operating in TappingMode). The probe 10 can also be driven towards and away from the polymerase 26 using a suitable actuator 16 also controlled by the computer 14. It should be noted that rather than being configured for driving the probe 10 towards the polymerase 26 as illustrated, the AFM could be configured for mounting a glass cell 34 (detailed below) on a moveable XY stage (not shown) so that the XY stage can be used to translate the sample relative to the probe 10.

Probe movement is monitored by a suitable probe detector, such as a displacement sensor 18 that may for example employ a laser and a photodetector as well as other components. As is known in the art, the signals from the sensor 18 can be used to determine probe oscillation amplitude, frequency, and phase, as well as other parameters, and to measure the probe-sample interaction based on the determined probe parameters. The computer 14 can use this measurement as a feedback signal to control the vertical probe-sample position via the actuator 16 so as to keep the probe-sample interaction constant during data acquisition. Finally, a suitable display device 24 is connected to the computer 14 and displays a humanly-discernible image of the measurement results in a visual image, such as a histogram.

The illustrated AFM is capable of operating in fluid so as to allow the AFM to obtain data during biological reactions. Preferably, a DNA/polymerase complex 50 is positioned in the AFM in a flow-through fluid chamber 32 of a glass cell 34. The AFM cantilever 8 and a probe tip 12 are submerged such that the height of the polymerase reaction fluid 36 is above the maximum deflection point of the cantilever 8. A polymerase 26 is disposed in the fluid chamber 32 for detection by the AFM. The polymerase 26 preferably is attached to a substrate 42 such as mica for reasons detailed below.

In use, the AFM operator prepositions the AFM probe 10 over a DNA/polymerase complex 50 to locate the complex. This positioning can be accomplished by several techniques including, but not limited to, the following. For instance, the operator can operate the AFM in scanning mode, as described above, until a DNA/polymerase complex 50 is located. Once the operator locates a complex, the operator switches the AFM from scanning mode to a data acquisition mode which may, for instance, comprise contact mode, TappingMode, or non-contact mode.

Alternatively, if a complex concentration in the cell is sufficiently high, a complex can be located simply by lowering the AFM probe into position with the expectation that there is a reasonable likelihood that the probe will be lowered into a complex. If the probe happens to miss a complex, the operator can simply raise the probe, move it slightly, and lower it again. If a complex is not located after a reasonable number of repetitions of this process, the probe 10 can be switched to a scanning mode to locate a complex.

Next, the AFM is placed in data acquisition mode to detect motions in the polymerase 26 during nucleotide incorporation into a growing polynucleotide chain 38 at a reaction site 40 and subsequent movement of the newly formed double-stranded DNA helix 48 or other motions associated with incorporation. The polymerase's motions generate a mechanical force that is reflected, either directly or indirectly, by motion of the AFM cantilever 8. The changes in motion may, for instance, be reflected by movement of a stationary probe, by reduction in oscillation amplitude of an oscillating probe, and/or by phase changes of an oscillating probe. The resulting changes in cantilever motion are detected by the AFM and indicate that a nucleotide has been incorporated into the growing DNA chain.

To determine which nucleotide is incorporated into the growing DNA chain during the polymerization reaction, at least one characteristic of the incorporation of nucleotides of the nucleotide type of interest is altered (i.e., flagged) to distinguish incorporation of nucleotides of the nucleotide type of interest (e.g., As) from nucleotides of the other types (e.g., Ts, Cs, or Gs). The flagging alters a characteristic of the detected motion such as (1) changes in average periods between motion detections or (2) changes in the magnitude of the motion. For instance, the average incorporation delay for nucleotides of the nucleotide type of interest may be flagged such that the average incorporation delay for nucleotides of the nucleotide type of interest is unique when compared to the average incorporation delay for nucleotides of other types.

Flagging can be achieved by several techniques including (1) altering the concentration of the nucleotides of the type of interest and (2) altering the size of the nucleotides of the type of interest. An example of such a flagging is using a one-half concentration of the nucleotide type of interest when compared to concentrations of other nucleotide types. Because it takes twice as long, on average, for a nucleotide of the nucleotide type of interest at a one-half concentration to come into the reaction site, this technique results in a doubling of the average incorporation delay for nucleotides of the nucleotide type of interest when compared to the other nucleotide types. Thus, flagging the nucleotide types of interest provides a method for distinguishing which nucleotide is incorporated into the growing DNA chain, and, hence, provides a basis for a method for determining the sequence of a DNA molecule.

This flagging and subsequent detection method can be used for several applications including (1) DNA sequencing and (2) mutation detection. For DNA sequencing, the method is used to determine the partial or complete sequence of a DNA molecule. These templates can include (but are not limited to) plasmid DNA molecules, viral DNA or RNA molecules, and polymerase chain reaction products.

For mutation detection, the method is typically (but not necessarily) used to determine a short sequence of a DNA region of interest (e.g., one to five nucleotides) containing a potential mutation site. For example, if a specific disease is caused by a C-to-T mutation at nucleotide 10 of gene 2 on chromosome 12, the method can be used to determine whether a C or T is present at this nucleotide. In this example, for a normal state, a C would be detected, whereas, for a diseased state, a T would be detected. Thus, the present invention can be used for mutation detection as well as DNA sequencing.

Several preferred exemplary embodiments of the basic process now will be detailed.

2. First Embodiment of Determining the Sequence of a DNA Template:

In a first embodiment, a plurality of reactions is performed, in which each reaction has a different nucleotide type of interest being flagged with a unique average incorporation delay characteristic. An example of this plurality of reactions embodiment is illustrated in the following Table A.

TABLE A

FOUR REACTION INCORPORATION DELAY DATA

| Reaction | Nucleotide | Nucleotide Type | delay type |
|---|---|---|---|
| 1 | 1 | Nucleotide type of interest | different delay |
| 1 | 2 | Another nucleotide type | delay |
| 1 | 3 | Another nucleotide type | delay |
| 1 | 4 | Another nucleotide type | delay |
| 2 | 1 | Another nucleotide type | delay |
| 2 | 2 | Nucleotide type of interest | different delay |
| 2 | 3 | Another nucleotide type | delay |
| 2 | 4 | Another nucleotide type | delay |
| 3 | 1 | Another nucleotide type | delay |
| 3 | 2 | Another nucleotide type | delay |
| 3 | 3 | Nucleotide type of interest | different delay |
| 3 | 4 | Another nucleotide type | delay |
| 4 | 1 | Another nucleotide type | delay |
| 4 | 2 | Another nucleotide type | delay |
| 4 | 3 | Another nucleotide type | delay |
| 4 | 4 | Nucleotide type of interest | different delay |

A preferred technique for the acquisition of the data tabulated in Table A and the sequencing of that data now will be detailed.

Figure 2:
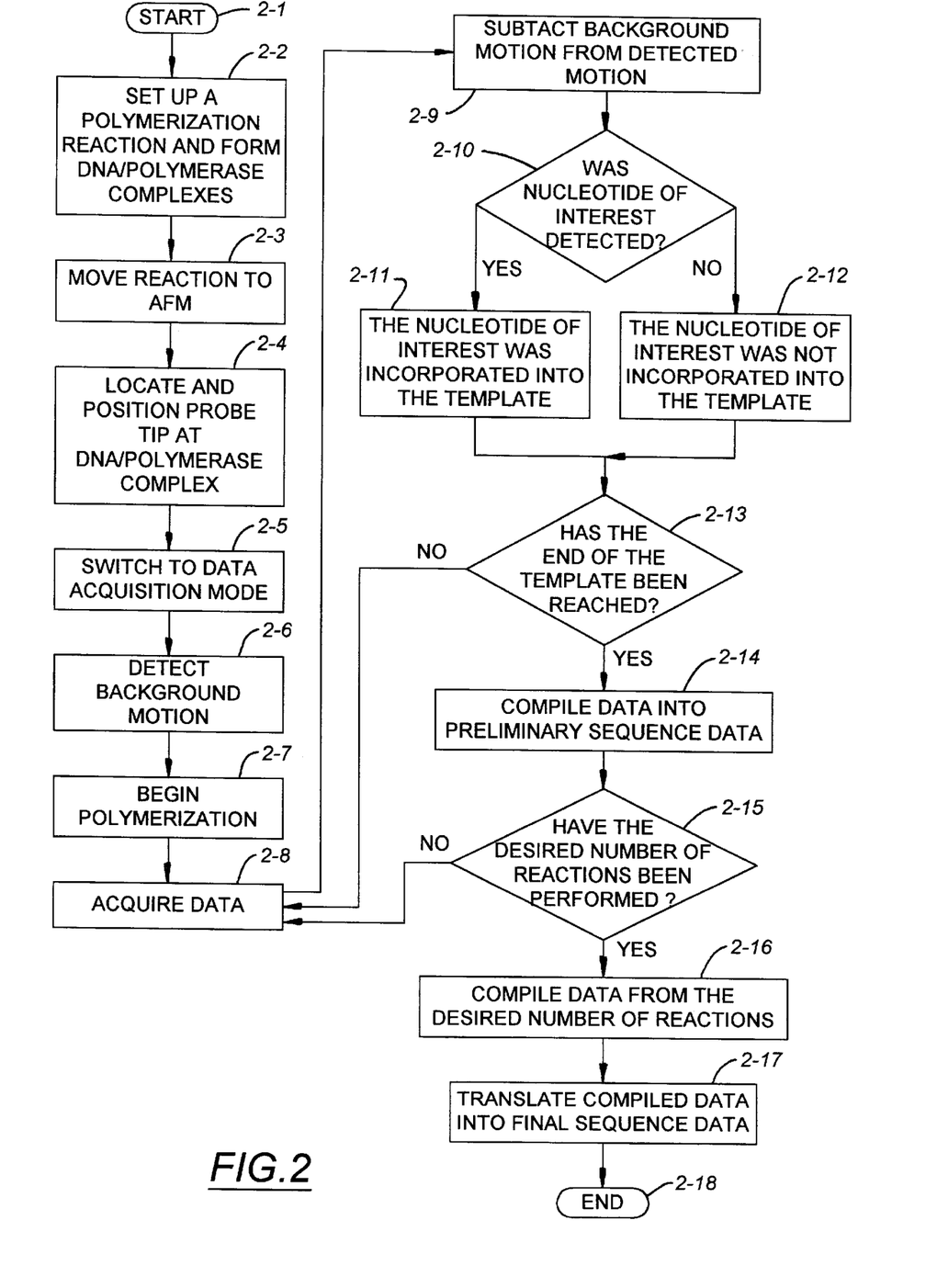
FIG. 2 is a flowchart of a DNA sequencing method performed in accordance with a first preferred embodiment of the invention in which a plurality of polymerization reactions is performed and in which incorporations of nucleotides of the nucleotide type of interest are flagged such that the incorporation of those nucleotides are unique when compared to incorporation of nucleotides of other types.

Referring to FIG. 2, in this embodiment, the determining of a DNA sequence proceeds from start in Step 2-1 to Step 2-2 in which a polymerization reaction is initiated and DNA/polymerase complexes are formed. The polymerization reaction is initiated by mixing together a polymerization buffer, a DNA template 30, a polymerase 26, appropriate salts (e.g., Taq DNA polymerase requires magnesium chloride), and nucleotides 28 (preferably, but not necessarily dNTPs). Typically, although not necessarily, a polynucleotide primer is also added to the reaction. Additionally, ATP may be added for purposes such as strand separation by DNA gyrase. The reaction is heated to a temperature appropriate for polymerization by the particular polymerase and retained at that temperature for a sufficient length of time to complete the polymerization reaction of interest. Heating is accomplished either by passive heating or active heating with a commercially available heating element. Heating can occur either before the reaction enters the fluid cell 34, after the reaction enters the fluid cell 34, or by causing pre-heated reaction components to continuously flow through the cell.

To facilitate data acquisition, the polymerase 26 is attached to a substrate 42, such as mica. This attachment stabilizes the polymerase's position with respect to the AFM by preventing the polymerase from floating away from the AFM. Attachment can be achieved either by non-covalent attachment or by covalent attachment. In non-covalent attachment the polymerase is dissolved in solution, and the polymerase is allowed to spontaneously adsorb to the substrate. Using this method, the density of adsorbed enzyme can be controlled by controlling the concentration of the polymerase in solution. In covalent attachment, a chemical linker or a coupling agent is used that couples the polymerase to the substrate. Additionally, attachment of the polynucleotide template 30 to the substrate 42 can be achieved by having an appropriate concentration of a divalent cation, such as $Zn^{++}$ or $Mg^{++}$.

The attachment of the polymerase 26 to the substrate 42 may occur either after or before the substrate 42 is inserted into the fluid cell 34 of the AFM. To attach the polymerase after substrate insertion, the substrate 42 is placed in the fluid cell 34, and a fluid containing the polymerase is added to the fluid cell. To attach the polymerase before substrate insertion, the polymerase is attached to the substrate at some other location, such as on a wet chemical bench. The latter technique (bench attachment) is more versatile because it permits polymerase/substrate assemblies to be made in advance and stored until they are to be retrieved for use.

The polymerization reaction preferably initially excludes at least one crucial reaction component, such as the nucleotides 28. This crucial reaction component(s) is subsequently added in Step 2-7, as detailed below. If the reaction is set up outside the AFM, it is then moved into the AFM in Step 2-3.

Additionally, in Step 2-2, the nucleotide type of interest is also flagged. Flagging can be achieved, for example, by controlling the concentration of the nucleotides of the nucleotide type of interest when compared to the concentration of other nucleotides. For example, if A is the nucleotide type of interest, the A concentration can be lowered to one-half the concentration of the other nucleotides to achieve an average incorporation delay that will take approximately twice as long as the average incorporation delay for the other nucleotides. This longer average incorporation delay of the nucleotide type of interest can be referred to as a "long incorporation delay." The average expected delay for the other nucleotide types can be referred to as a "normal incorporation delay."

In Step 2-4, the AFM is used to locate a DNA/polymerase complex as described above. Once the complex is located, the probe tip 12 of the AFM is positioned at the complex, as illustrated in FIG. 1. The AFM is then switched to data acquisition mode in Step 2-5. Both the polymerase 26 and the AFM generate background motion during data acquisition. If not accounted for, these background motions could interfere with data acquisition. However, by initiating data acquisition in Step 2-5 prior to initiating the nucleotide reaction and detecting background motions in Step 2-6, the method permits differentiation of motion due to the polymerization reaction and background motions and hence accounts for background noise.

Next, the reaction component, withheld in Step 2-2, is added in Step 2-7 to begin the polymerization reaction. Data acquisition of polymerization motions then begins in Step 2-8. These motions occur when a nucleotide 28 is incorporated into the growing DNA chain 38, and the newly formed double-stranded DNA helix 48 translocates through the reaction site 40 of the polymerase 26. The DNA translocates in a single direction 46, as is shown in FIG. 1. These motions generate a mechanical force that is reflected, either directly or indirectly, by changes in the motion of the AFM cantilever 8 as described above. The changes in cantilever motion are detected and can be recorded. The background motion from the polymerase and AFM, having been measured in Step 2-6 as described above, is subtracted from the acquired data in Step 2-9 to obtain a true indication of probe reaction to nucleotide incorporation. The incorporation delay for the nucleotide therefore can be detected at this time.

Next, in Step 2-10, based on the detected incorporation delay, the method determines whether or not incorporation of a nucleotide of the nucleotide type of interest has occurred. This determination is based upon whether the detected incorporation delay is a long incorporation delay or a normal incorporation delay. For each location of interest, if a long incorporation delay is detected, then the answer to the question posed in Step 2-10 is "yes," and in Step 2-11, the method determines that a nucleotide of the nucleotide type of interest was incorporated into the growing polynucleotide chain at that location. Thus, if A is the nucleotide of interest and the method detects a long incorporation delay in Step 2-10, then, in Step 2-11 the method determines that an A was incorporated into the growing polynucleotide chain at that position. On the other hand, if a normal incorporation delay is detected, then the answer to the question posed in step 2-10 is "no" and in Step 2-12, the method determines that the nucleotide of interest was not incorporated, (i.e., that an "A" was not incorporated).

In Step 2-13 the method determines whether the desired end of the template has been reached. If the desired end has not been reached, then Steps 2-8 through 2-13 are repeated until the method reaches the end of the template, at which point the method proceeds to Step 2-14.

In Step 2-14, for each reaction and each location of interest, the method compiles data into preliminary sequence data. For each location of interest on the growing polynucleotide chain, the data obtained from the method is generated in the format of: "nucleotide of interest was incorporated" or "nucleotide of interest was not incorporated." For example, using the 5'-ATCGG-3' example, the preliminary data for the A reaction would read: "A, not A, not A, not A, not A."

Next, the method may be repeated for a desired number of reactions. In each reaction, a different nucleotide of interest is flagged by controlling the concentration of that nucleotide type to be different from the concentration of the other nucleotide types, and Steps 2-8 through 2-15 are repeated until it is determined in Step 2-15 that all desired reactions have occurred. Once it has been determined that all desired reactions have occurred, then the cycling back to Step 2-8 ceases.

In Step 2-16, the data from the desired reactions is compiled (as reflected in Table A), and next, in Step 2-17, the method translates the complied data into final sequence data by aligning, based on location in the DNA template, the data compiled in each reaction in Step 2-14. Specifically, for the above example, 5'-ATCGG-3', if the G, A, T, and C reactions include data from locations one through five, these data are lined up, putting preliminary sequence data from each location in the corresponding location. Next, examining each location separately, the method compiles the data.

For the above example, 5'-ATCGG-3', in the first position, where an A is located, the reaction would read: G reaction: not G, A reaction: A, T reaction, not T, C reaction: not C. Compiling this data, the method determines that position one is an A. Likewise, for position two, where a T is located, the data would read: G reaction: not G, A reaction: not A, T reaction: T, and C reaction: not C. Compiling this data, the method determines that position two is a T. For the above example, compiling and translating the entire five nucleotide length yields a final DNA sequence of "ATCGG." The method then ends at Step 2-18.

Figure 3:
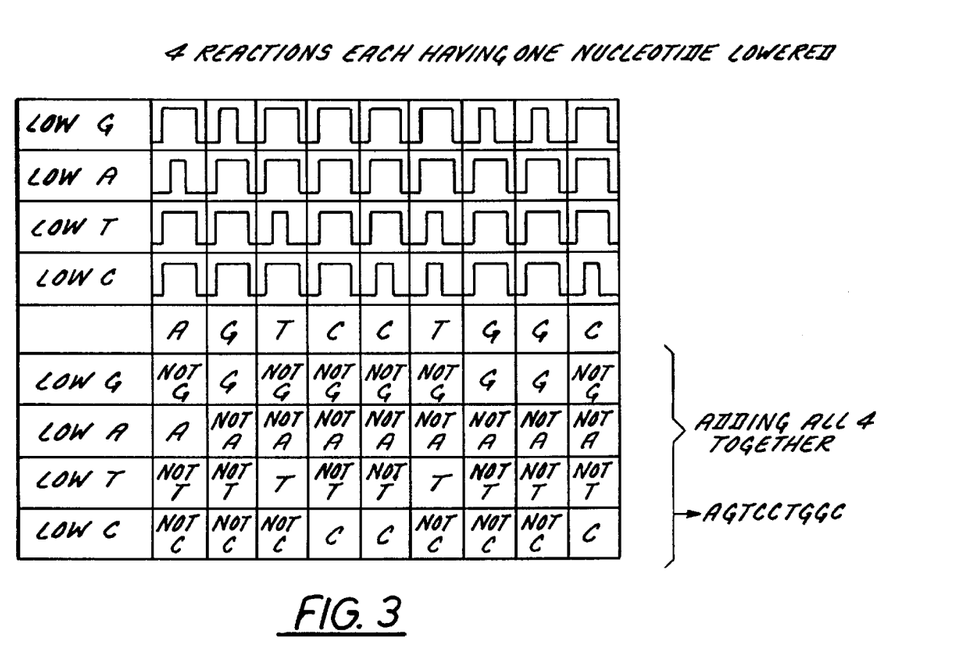
FIG. 3 is a graph illustrating the profile of data obtained from an AFM detection of flagged incorporation of nucleotides into a growing DNA chain during a polymerization reaction performed in accordance with the first embodiment.

The exemplary data output obtained from performing Steps 2-1 through 2-18 in this first preferred embodiment is tabulated in Table A and illustrated graphically in FIG. 3. Specifically, FIG. 3 illustrates the compilation of data from Step 2-16 and translation of the compiled data into final sequence data from Step 2-17. The data analysis step detailed above may be performed either in real-time or at a later convenient time.

3. Second Embodiment of Determining the Sequence of a DNA Template:

In a second preferred embodiment, only one reaction is performed in which the concentration of each nucleotide type is controlled to produce a unique average incorporation delay when compared to the other unique average incorporation delays of all other nucleotide types. An example of this one reaction embodiment is tabulated in Table B.

TABLE B

| ONE REACTION INCORPORATING DELAY DATA | | | |
|---|---|---|---|
| Reaction | Nucleotide | Nucleotide Type | delay type |
| 1 | 1 | first type of interest | unique delay 1 |
| 1 | 2 | second type | unique delay 2 |
| 1 | 3 | third type | unique delay 3 |
| 1 | 4 | fourth type | unique delay 4 |

Figure 4:
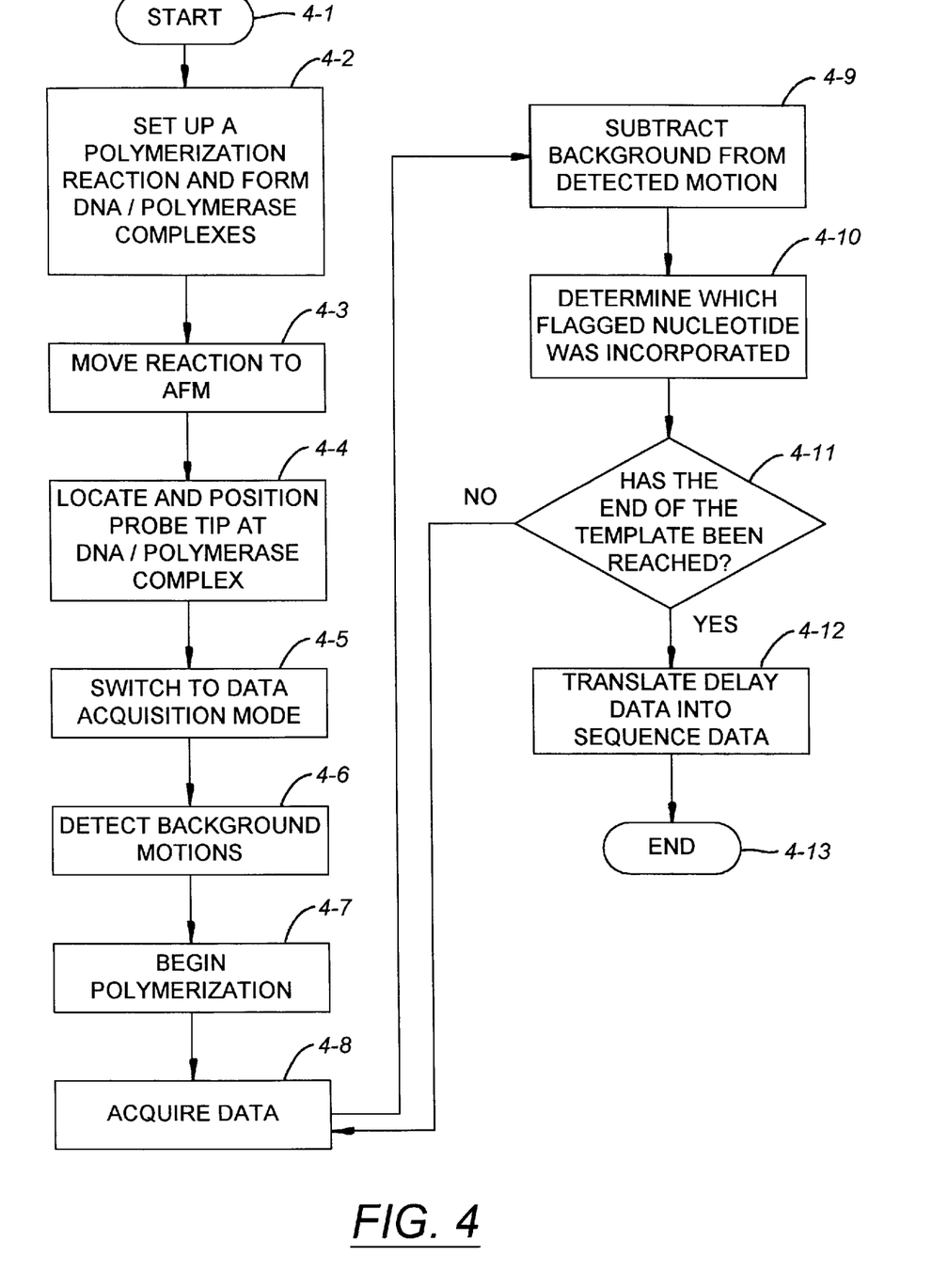
FIG. 4 is a flowchart of a DNA sequencing method performed in accordance with a second preferred embodiment of the invention in which a polymerization reaction is performed with the flagging of a plurality of nucleotide types of interest such that each nucleotide incorporation type is distinguishable from the incorporation of other nucleotide types.

Referring to FIG. 4, determining a DNA sequence in accordance with this embodiment proceeds from start in Step 4-1 to Step 4-2 in which a polymerization reaction is set up and DNA/polymerase complexes are formed. As in the first embodiment, this reaction preferably excludes at least one crucial reaction component, such as the nucleotides. If the reaction is set up outside the AFM, it is then moved into the AFM in Step 4-3. In Step 4-4, as described above, the AFM is operated until a DNA/polymerase complex is located. Once the DNA/polymerase complex is located, the probe tip 12 is positioned at the complex, and the AFM is then switched to data acquisition mode in Step 4-5. In Step 4-6, the AFM detects background motions.

Figure 5:
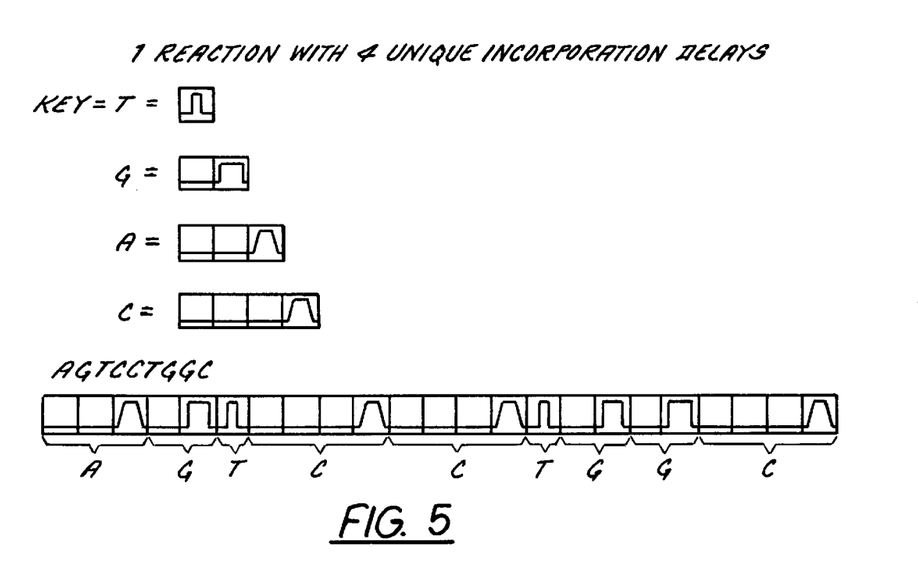
FIG. 5 is a graph illustrating the profile of data obtained from detection of flagged incorporation of nucleotides into a growing DNA chain during a polymerization reaction performed in accordance with the second embodiment.

To start the polymerization reaction, the reaction component(s), withheld in Step 4-2, is added in Step 4-7. Data acquisition then begins in Step 4-8, and a nucleotide incorporation is detected. In Step 4-9, the background motion is subtracted from the acquired data to obtain a true indication of probe reaction to nucleotide incorporation. The incorporation delay for the detected nucleotide can then be calculated. In Step 4-10, a determination is made as to which incorporation delay was detected in Step 4-8 and, hence, of which nucleotide was incorporated. In Step 4-11, the method determines whether the end of the template has been reached. If it has not, then Steps 4-8 through 4-11 are repeated. Data from Step 4-10 is then translated into sequence data in Step 4-12. In this embodiment, data are expressed in terms of unique average incorporation delays. For example, in the DNA template example 5'-CCGAT-3' having the reverse complement 5'-ATCGG-3', if delay 1 represents A, delay 2 represents T, delay 3 represents C, and delay 4 represents G, then the data would read, "delay 1, delay 2, delay 3, delay 4, delay 4." The method then ends at Step 4-13. The data output obtained from performing Steps 4-1 through 4-13 in this second preferred embodiment is tabulated in Table B and is illustrated in FIG. 5. Specifically, FIG. 5 illustrates the determination of which nucleotide delay occurred from Step 4-10 and the translation of this data into sequence data from Step 4-12. The data analysis steps detailed above may be performed either in real-time or later at a convenient time.

The same method can be used to detect mutations by determining which nucleotide is present at a single location or at a limited number of locations. Additionally, using the method for DNA sequencing, the method can be used to determine which nucleotide is present at many locations.

For all embodiments, by detecting the sequence directly off the polymerase, the DNA sequencing may be advantageously performed in real time. This real-time detection of DNA polymerization accomplishes the important benefit of providing a rapid, automated, DNA sequencing method. The rapid speed of the present invention therefore is limited only by the detection rate of the AFM, which is currently typically one kilohertz (or 1000 data points per second). Acquiring sequence data by this method requires two-to-three data points per nucleotide. The speed of a typical polymerase reaction is 30 incorporations of nucleotides per second for RNA polymerases and 300 to 3000 incorporations of nucleotides per second for DNA polymerases. Thus, depending upon the polymerase used, the rate of the polymerization reaction may need to be reduced to a speed below the detection rate of the AFM. However, because attachment of a polymerase to mica, and/or the polynucleotide involved in the reaction, slows the incorporation rate, a further reduction may not be necessary. Reduction, if required, can be accomplished in several ways, including altering the polymerase concentration, lowering the reaction temperature, and varying the degree to which the polynucleotide involved in the reaction is bound to the mica.

Additionally, for all embodiments, the signal to noise ratio for this inventive method (here, the ratio of polymerization motion to background motion) is higher than signal to noise ratio for the method disclosed by Holzrichter in U.S. Pat. No. 5,620,854. Incorporation detection therefore is facilitated.

4. Additional Aspects of the Invention:

Previous DNA sequencing chemistries such as those proposed by (1) Maxam and Gilbert and (2) Sanger et al., obtained data from multiple enzymes and multiple templates. Therefore, most inaccuracies in sequence data stemming from both the polymerase itself and from the method were diluted by correct sequence data, and multiple runs were not necessary. Polymerases have occasional inherent errors in nucleotide incorporation where DNA base paring rules (discussed supra), are violated. For example, such an error would occur if a DNA template contains a G at a certain location, and base pair rules dictate that the polymerase should incorporate a C, but the polymerase instead incorporates a T. Error rates for various polymerases are generally known in the molecular biology art.

However, using an AFM to detect nucleotide incorporation from a single molecule of polymerase does not dilute out inaccurate data, because only a single set of data from a single polymerase molecule is obtained in each sequence run. To correct for this effect and to ensure accurate sequence data, the present invention has the ability to use data acquired from multiple sequence runs. For instance, after Steps 2-1 through 2-15 in the first embodiment or Steps 4-1 through 4-11 in the second embodiment are performed on a first polymerase molecule, the AFM may be relocated to a second polymerase molecule, and Steps 2-4 through 2-14 or Steps 4-4 through 4-10 may be repeated for multiple polymerase molecules. Alternatively, the AFM probe may remain on the originally-located polymerase molecule, and the AFM may detect polymerization motions from another DNA template that comes into the reaction site of the original polymerase molecule. The data obtained from the multiple runs may be compiled to generate a consensus sequence of the DNA sequence, which contains the nucleotide most commonly found for each position in the DNA chain.

For example, for the above DNA sequence of "ATCGG," multiple sequence runs might read, "ATCGG," "ATCGT," "ATCGG," "ATCGG," and "ATCGG." Note that the second run contains an error at the last position (i.e., a T instead of a G). A compiled consensus sequence contains "ATCGG," the presumably correct sequence.

Using multiple sequence runs also corrects for inaccuracies stemming from incorrect conclusions concerning incorporation delay. For example, in the embodiment where nucleotide concentrations are controlled such that incorporation delays are used to determine which nucleotide type was incorporated, a nucleotide of the nucleotide type of interest occasionally will be in close proximity to the reaction site. As a result, a nucleotide of the nucleotide type of interest could be incorporated more quickly than expected. This shorter-than-expected delay might erroneously shift the incorporation delay from a long incorporation delay to a normal incorporation delay which might be translated into an incorrect determination of a different nucleotide type. Thus, an error in polymerization will not occur, but an error in detection will occur. This potential inaccuracy in detection can be avoided or at least alleviated by using data from multiple runs and compiling this data into a consensus sequence.

Another important aspect of the present invention is its ability to use average incorporation delays that are outside of the range in which natural variations in average incorporation delays would obscure the acquired data. A typical polymerization reaction has some variability in delays for individual nucleotides. For example, if (1) the A nucleotide is the nucleotide type of interest, (2) the polymerization reaction is performed such that the theoretical incorporation delays are one millisecond for G, T, and C, and two milliseconds for A, and (3) there is a fifty percent variation in incorporation time (i.e., the variability rate), then the G, T, and C acquired delay data might vary from 0.5 to 1.5 milliseconds, and the A might vary from 1.0 to 3.0 milliseconds. Thus, the acquired data might actually read: G=1.5 milliseconds, T=1 millisecond, C=0.5 milliseconds, and A=1 millisecond. These acquired delay data points are not interpretable into the correct DNA sequence because the delays are not distinct for the nucleotide type of interest when compared to other nucleotide types. Thus, correct DNA sequence data cannot be obtained if the variability rate coupled with the theoretical average incorporation delay generates acquired delays that are not distinct when nucleotide types of interest are compared to other nucleotide types. This potential problem can be avoided simply by suitably controlling the concentration of the nucleotide type of interest, (e.g., by reducing the A concentration further so that the area of incorporation delay for A is four milliseconds).

Yet another important feature of the present invention is its ability to eliminate or to at least minimize secondary structure in the DNA template. A DNA template, being an at least partially single-stranded molecule, can form base pairs with itself. For example, a DNA sequence can bend backward and form C-G base pairs and A-T base pairs within the molecule, thus forming secondary structure. Due to the bulky nature of the secondary structure, this structure can inhibit movement of the DNA template through the reaction site of the polymerase. This inhibited movement might generate problems, including (1) altering incorporation delays such that one nucleotide type's incorporation delay mimics the incorporation delay of another nucleotide type and (2) stopping the polymerization reaction altogether.

The invention addresses these secondary structure problems in several ways. For instance, the polymerization can be performed at a temperature that is high enough to cause the secondary structure to disassociate, thus, returning the DNA template to a single-stranded molecule without secondary structure. Alternatively, a chemical compound, such as spermidine or polyethylene glycol, can be added to the polymerase reaction to disallow formation of secondary structure. Adding chemical compounds to reduce secondary structure in DNA templates in polymerase reactions is practiced widely in the art of molecular biology.

5. Additional Embodiments.

The method of this invention can be practiced in several other embodiments. For instance, the core method can be practiced by initiating data acquisition either (1) starting at a beginning of a DNA template or (2) starting at any location along a DNA template. Several methods can be employed to initiate data acquisition at the beginning of a DNA template. First, as described above, at least one of the polymerase reaction components can be withheld from the reaction until the AFM detects the DNA/polymerase complex and is ready to acquire data. After the complex is detected, the withheld component can then be added, and polymerization will begin.

Second, the polymerase reaction temperature can be cycled such that the polymerization will not proceed until the appropriate temperature is reached. An example of temperature cycling is to (a) start the reaction at a high temperature at which the DNA/polymerase complex will not form (i.e., a disassociation temperature); (b) reduce the reaction temperature to a low temperature at which the complex will form, but the polymerization will not occur, or will occur only negligibly (i.e., a hybridization temperature); and (c) increase the reaction temperature to an intermediate temperature such that the polymerization reaction will optimally occur (i.e., a polymerization temperature). In this embodiment, the probe of the AFM is placed at the complex after the reaction reaches the hybridization temperature, and the data acquisition step begins after the reaction reaches the polymerization temperature. This embodiment additionally allows for the detection of replicate DNA templates from the same polymerase molecule in multiple runs because the temperature cycling can be used to produce multiple runs. Specifically, to generate multiple runs, the first run is performed by cycling the reaction temperature from 1) the disassociation temperature, 2) to the hybridization temperature, and 3) to the polymerization temperature. The second run is then performed by repeating this cycling of the three temperatures. Each time that the disassociation temperature is reached, any previous DNA/polymerase complexes disassociate. Next, at the hybridization temperature, a new DNA/polymerase complex is formed. Once complexes are formed, the AFM may be moved to detect a new complex. Finally, at the polymerization temperature, a new polymerization reaction is performed. During polymerization, the AFM may detect incorporation of nucleotides into the growing DNA chain. Thus, this temperature cycling provides a way to obtain data from multiple polymerization reactions.

The present invention provides several advantages over prior methods for determining the sequence of a DNA template, including the chemistry, the instrumentation, and real-time detection. First, the chemistry of the present invention involves a polymerization reaction, whereas previous methods involved other chemistries such as a sequencing reaction. Second, the inventive method uses an AFM or another local sensitive force detector, whereas previous methods used other instrumentation, typically including electrophoretic equipment. Third, the present invention involves detecting DNA sequence in real-time, whereas other methods required first performing the appropriate chemistries (usually a sequencing reaction), then electrophoresising the products of the sequencing reactions, and then detecting the reactions and determining the DNA sequence.

Many changes and modifications could be made without departing from the spirit and scope of the invention. Such changes and modifications will become apparent from the appended claims.

I claim:

1. A method comprising:
   (A) incorporating nucleotides of more than one nucleotide type into a growing polynucleotide chain by a polymerase during a polymerase reaction in which the order of incorporation is driven by base pair rules and a delay occurs between each successive nucleotide incorporation;
   (B) controlling at least one characteristic of the incorporation of at least one nucleotide type of interest into the growing polynucleotide chain such that the concentration of a nucleotide of interest is different from the concentration of at least one other nucleotide and wherein the incorporation delay of the nucleotide of interest is different from the average incorporation delay for nucleotides of at least one other nucleotide type;
   (C) locating the polymerase with a local sensitive force detector;
   (D) detecting by using the local sensitive force detector, a motion associated with the nucleotide incorporation into the growing polynucleotide chain; and
   (E) producing data using a computer to transform detected incorporation data into nucleofide data.

2. A method as defined in claim 1, wherein the locating step comprises,
   (A) operating the detector in a scanning mode to locate a polynucleotide/polymerase complex, and then
   (B) switching from the scanning mode to a data acquisition mode in which a probe tip of the detector is placed at the polynucleotide/polyinerase complex.

3. A method as defined in claim 1, wherein the locating step comprises operating the detector in an approaching mode to locate a polynucleotide/polymerase complex,
   and then
      if a complex is found, then switching from the approaching mode to a data acquisition mode in which a probe tip of the detector is placed at the polynucleotide/polymerase complex, or
      if a complex is not found, then switching from the approaching mode to a scanning mode to locate a polynucleotide/polymerase complex.

4. A method as defined in claim 1, wherein the locating step comprises operating the detector in an approaching mode to locate a polynucleotide/polymerase complex,
   and then
      if a complex is found, then switching from the approaching mode to a data acquisition mode in which a probe tip of the detector is placed at the polynucleotide/polynerase complex, or
      if a complex is not found, then re-engaging to locate a polynucleotide/polymerase complex.

5. A method as defined in claim 1, wherein the detecting step comprises using a probe of the detector to detect a motion occurring when a nucleotide is incorporated into the growing polynucleotide chain and a newly formed structure translocates through a reaction site of the polynerase.

6. A method as defined in claim 5, wherein the detector comprises an atomic force microscope (AFM) and wherein the motion generates a mechanical force that is reflected by a motion of a cantilever of the AFM.

7. A method as defined in claim 1, wherein, during the incorporating step, incorporation delays occur between successive nucleotide incorporations, and wherein the controlling step comprises controlling an average incorporation delay for nucleotides of the nucleotide type of interest to differ from an average incorporation delay for nucleotides of at least one other nucleotide type.

8. A method as defined in claim 7, wherein the controlling step comprises controlling the average incorporation delays for nucleotides of all nucleotide types other than the nucleotide type of interest to be at least substantially the same as one another.

9. A method as defined in claim 8, further comprising controlling an average incorporation delay for nucleotides of at least two nucleotide types of interest to differ from an average incorporation delay for nucleotides of at least one other nucleotide type.

10. A method as defined in claim 1, wherein the controlling step comprises controlling an amplitude of a motion as measured by a probe detector occurring when a nucleotide is incorporated into the growing polynucleotide chain and a newly formed structure translocates through a reaction site of the polymerase.

11. A method as defined in claim 1, wherein the controlling step comprises conjugating a nucleotide of the nucleotide type of interest with a molecule.

12. A method as defined in claim 1, wherein the controlling step comprises:

(A) performing a plurality of polymerization reactions, and (B) during each of the polymerization reactions, controlling the at least one characteristic of the incorporation of a different nucleotide type of interest such that the incorporation of a nucleotide of the nucleotide type of interest is distinguishable from the incorporation of nucleotides of all other nucleotide types, and further comprising determining, based on the controlling and detecting steps, which nucleotide type was incorporated into the growing polynucleotide chain during the incorporating step.

13. A method as defined in claim 12, wherein the determining step comprises:

(A) examining each of the reactions separately, and, for each of the reactions, (1) detecting whether or not a nucleotide of the nucleotide type of interest for that reaction is incorporated and (2) generating a set of data, and (B) adding a plurality of sets of data together to generate nucleotide sequence data for all of the data sets.

14. A method as defined in claim 1, wherein, during the controlling step, at least one characteristic of the incorporation for the nucleotide type of interest is unique when compared to the corresponding characteristics of the incorporation for all other nucleotide types in the polymerization reaction.

15. A method as defined in claim 14, further comprising determining, based on the controlling and detecting steps, which nucleotide type was incorporated into the growing polynucleotide chain during the detecting step, wherein the polymerization reaction is performed in a single reaction and a plurality of nucleotide types each have a unique incorporation characteristic when compared to corresponding incorporation characteristics of other nucleotide types, wherein the detecting step comprises detecting the unique incorporation characteristic of each of the nucleotides types, and wherein the determining step comprises determining, from the unique incorporation characteristic, which nucleotide type was incorporated into each location of interest of the growing polynucleotide chain.

16. A method as defined in claim 1, wherein the detecting steps further comprises subtracting background noise from detected probe operating parameters, the background noise arising from at least one of unintended probe motion and enzyme motion.

17. A method as defined in claim 1, wherein the incorporating step comprises controlling the polymerization reaction such that a rate of the polymerization reaction permits detection of incorporations.

18. A method as defined in claim 1, wherein the incorporating step comprises controlling the polymerization reaction such that a rate of the polymerization reaction is outside of a range in which natural variations in average incorporation delays would obscure acquired data.

19. A method as defined in claim 1, wherein the incorporating step comprises using a polymerase that is attached to a substrate.

20. A method as defined in claim 1, wherein the incorporating step comprises starting the incorporation at the beginning of the growing polynucleotide chain.

21. A method as defined in claim 1, further comprising repeating the incorporating, controlling, and detecting steps for a plurality of polymerase reactions.

22. A method as defined in claim 1, wherein the incorporating step comprises controlling the temperature of the polymerase reaction.

23. A method as defined in claim 1, further comprising detecting mutations during the polymerase reaction by using the method to determine which nucleotide type was incorporated into the growing polynucleotide chain for a small number of nucleotides.

24. A method as defined in claim 1, wherein the detector comprises an atomic force microscope (AFM).

25. A method as defined in claim 1, wherein the detecting step comprises detecting a motion of the polymerase.

26. A method comprising:

(A) incorporating nucleotides of more than one nucleotide type into a growing polynucleotide chain by a polymerase during a polymerase reaction in which the order of incorporation is driven by base pair rules;

(B) controlling at least one characteristic of the incorporation of at least one nucleotide type of interest into the growing polynucleotide chain such that the incorporation of nucleotides of the nucleotide type of interest is distinguishable from the incorporation of nucleotides of at least one other nucleotide type;

(C) locating the polymerase with a local sensitive force detector;

(D) detecting using the local sensitive force detector, a motion associated with the nucleotide incorporation into the growing polynucleotide chain;

(E) producing data using a computer to transform detected incorporation data into nucleotide data; and (F) withholding at least one reaction component until a time just prior to a time at which data acquisition begins.

27. A method comprising:

(A) incorporating nucleotides of more than one nucleotide type into a growing polynucleotide chain by a polymerase during a polyrnerase reaction in which the order of incorporation is driven by base pair rules;

(B) controlling at least one characteristic of the incorporation of at least one nucleotide type of interest into the growing polynucleotide chain such that the incorporation of nucleotides of the nucleotide type of interest is distinguishable from the incorporation of nucleotides of at least one other nucleotide type;

(C) locating the polymerase with a local sensitive force detector in Tapping Mode;

(D) detecting using the local sensitive force detector, a motion associated with the nucleotide incorporation into the growing polynucleotide chain; and (E) producing data using a computer to transform detected incorporation data into nucleotide data.

28. A method comprising:

(A) incorporating nucleotides of more than one nucleotide type into a growing polynucleotide chain by a polymerase during a polymerase reaction in which the order of incorporation is driven by base pair rules;

(B) controlling at least one characteristic of the incorporation of at least one nucleotide type of interest into the growing polynucleotide chain such that the incorporation of nucleotides of the nucleotide type of interest is distinguishable from the incorporation of nucleotides of at least one other nucleotide type and wherein secondary structure of a polynucleotide template formed by the incorporation is minimized;

(C) locating the polymerase with a local sensitive force detector;

(D) detecting using the local sensitive force detector, a motion associated with the nucleotide incorporation into the growing polynucleotide chain; and (E) producing data using a computer to transform detected incorporation data into nucleotide data.

* * * * *